United States Patent [19]

O'Leary et al.

[11] Patent Number: 4,460,008
[45] Date of Patent: Jul. 17, 1984

[54] INDEXING CONTROLLER APPARATUS FOR COOLING WATER TOWER SYSTEMS

[76] Inventors: Richard P. O'Leary, 331 Louella Ave., Wayne, Pa. 19087; Robert V. Morris, 221 S. 14th, Muskogee, Okla. 74401

[21] Appl. No.: 452,672

[22] Filed: Dec. 23, 1982

[51] Int. Cl.³ ............................................. G05D 11/08
[52] U.S. Cl. ............................................ 137/93; 137/5
[58] Field of Search ...................... 137/5, 93; 324/439, 324/443, 448

[56] References Cited

U.S. PATENT DOCUMENTS

| | | | |
|---|---|---|---|
| 3,410,292 | 11/1968 | Bennett et al. | 137/5 |
| 3,428,557 | 2/1969 | Rivers | 137/5 |
| 3,918,469 | 11/1975 | Zamboni et al. | 137/5 |
| 4,091,833 | 5/1978 | Ellis et al. | 137/93 |
| 4,273,146 | 6/1981 | Johnson | 137/5 |

Primary Examiner—Martin P. Schwadron
Assistant Examiner—James R. Shay
Attorney, Agent, or Firm—Caesar, Rivise, Bernstein & Cohen, Ltd.

[57] ABSTRACT

A control system and method of controlling the cycling of water in a cooling tower system having a course of make-up water of variable conductivity.

The control system apparatus includes respective probes for sensing tower water conductivity and make-up water conductivity. The probes provide signals to a controller unit. Desired cooling system water conductivity parameters an input into the controller unit. The controller unit serves to proportionately adjust the trip point at which dumping of the cooling tower water occurs based upon the sensed water conductivities and the input parameters to maintain a predetermined Langelier's number(s). Means are provided to display system conditions and to effect calibrations of the system.

The method entails establishing an indexing factor based upon the cooling water parameters and the desired Langelier's number(s) and using that indexing factor for adjusting the trip point.

15 Claims, 4 Drawing Figures

INDEXING CONTROLLER APPARATUS FOR COOLING WATER TOWER SYSTEMS

BACKGROUND OF THE INVENTION

This invention relates generally to cooling tower water control systems and more particularly to electrical control apparatus and a method for automatically and accurately controlling the cyclical blowdown operation of the system irrespective of changes in the conductivity of make-up water introduced into the system during blowdown.

As is known in water cooling tower systems minerals build up in the water due to evaporation as the water is cycled through the cooling tower. Various chemicals are used commercially to keep the minerals from salting out (i.e., scaling) since such action retards heat transfer, thereby decreasing the efficiency of the cooling operation. Moreover corrosion inhibiting chemicals are also introduced into the cooling water to prevent the water from becoming corrosive as it is oxygenated during the cooling operation. In order to maximize the number of cycles cooling water can be circulated before its mineral concentration builds up to excessive levels. It is a common practice to try and maintain the water at a desired Langeliers saturation index that is relatively high, e.g., +2.5 or low, e.g., −0.5, through the use of chemical additives. Such action maintains the alkaline minerals in solution, thereby precluding corrosion, and without the deleterious effects of scaling.

Each time that the water is cycled through the system the total dissolved solids build up further and hence the conductivity of the water increases. When the conductivity of the water has reached a predetermined maximum (at which scaling could occur even with the use of the scale retardant chemicals in the water) coolant water is dumped from the system and replaced with what is known as "make-up" water. In addition due to the dumping of some of the cooling tower water (a process frequently referred to as "blow-down") additional chemical additives have to be introduced to take the place of the proportion of those chemicals which was lost with the dumped water so that the chemical concentration stays the same.

Heretofore electronic devices have been used to automatically effect "blow-down" when the concentration of the water in the cooling tower reaches a predetermined maximum (called the trip point). To that end, such devices have been designed to automatically actuate a solenoid valve controlling the dumping of water to the drain when a predetermined water concentration is detected. The means for detecting the predetermined concentration normally consists of an electrically sensing conductivity probe located in the cooling water system. The trip point, is normally established by utilizing the Langeliers Saturation Index to calculate the conductivity which would occur after a predetermined number of cycles of concentration. In order to determine the maximum concentration at the predetermined cycles of concentration the conductivity of the input water has to be known.

Morr Control, Inc. of Muskogee, Okla. has sold conductivity controllers like those described heretofore, under the designation "Cyclotron". That device includes a conductivity sensing probe in the cooling tower circulation loop for monitoring the tower water as it is cycled through the system and another similar probe in the "make-up" water input line to the cooling tower. Both probes are connected to an electronic unit or controller for measuring and displaying the conductivity of the water as sensed by the associated probes. The Cyclotron controller also includes adjustable means for establishing the predetermined number of times that the water in the system is allowed to cycle through before the water is dumped. That cycle number is used by the Cyclotron controller to act as a multiplier of the concentration of the make-up water to establish the trip point for the probe sensing the cooling tower water conductivity.

While the Cyclotron device as described above is perfectly suitable for cooling tower systems in which the make-up water remains relatively constant, such a controller system has substantial limitations if the make-up water conductivity changes substantially. For example, if the Cyclotron controller is set up for make-up water to have a maximum conductivity of 60 micromhos and to be cycled five times, the maximum conductivity in micromhos, that is the trip point, will be three hundred at a predetermined Langeliers saturation index. If the input water conductivity increases to three hundred micromhos then the trip point of the system would be the conductivity of the make-up water concentrated through five cycles of operation before blowdown (fifteen hundred micromhos). Before the water reaches that concentration it would more than likely begin scaling. Thus, with prior art conductivity measuring systems, like the Cyclotron, substantial changes in make-up water conductivity cannot be accommodated to maintain automatic control.

OBJECTS OF THE INVENTION

Accordingly, it is a general object of the instant invention to provide a conductivity control system for cooling tower water systems which overcomes the disadvantages of the prior art.

It is a further object of the instant invention to provide an automatic electronic control system for use in cooling tower water control systems to effect automatic recycling of tower water, irrespective of changing make-up water conditions.

It is a further object of the instant invention to provide an electronic system which is simple in construction and accurate and efficient in operation to control the bleeding and replacement of make-up water in a cooling tower system having a source of make-up water of variable conductivity.

SUMMARY OF THE INVENTION

These and other objects of the instant invention are achieved by providing a solid state control system for use in a cooling tower water system having a supply of make-up water and means for enabling water to be drained from said system. The control system comprises signals generating means for producing a periodic signal, first conductivity sensing probe means coupled to the signal generating means and adapted for disposition in the cooling tower water to provide a first signal proportional to the conductivity of the tower water, and second conductivity sensing probe means coupling to the signal generating means and adapted for disposition in the make-up water supply to said cooling tower to provide a second signal proportional to the conductivity of the make-up water. The system also comprises display means for displaying cooling water conductivities, first and second selectively actuable calibration means for calibrating the display means to said first conductivity sensing probe means and said second conductivity sensing probe means, respectively, and selector switch means for selectively providing signals produced by the control system to the display means to display conductivity readings. Third circuit means is coupled to the second conductivity sensing probe for receipt of the second signal. The second input of the third circuit means comprises an adjustable signal. The third circuit means subtracts the second signal from the first signal to produce a delta signal. The delta signal is coupled, via the selector switch means, to the display means to display the delta signal. Fourth circuit means are provided connected to the third circuit means and include fourth selectively adjustable means for producing a product signal equal to the product of the delta signal and a value established by the fourth selectively adjustable means. Fifth circuit means are provided connected to the fourth circuit means and to the selector switch means. The fifth circuit means includes a pair of inputs and fifth selectively adjustable means for producing a fifth signal. The fifth signal serves as one of the inputs to the fifth circuit means while the product signal serves as the other of its inputs. The fifth circuit means adds the input signals to produce an output signal. The output signal is coupled by the selector switch means to the display means for display thereof. Comparator means are provided connected to the fifth circuit means and arranged for receipt of the output signal and the first signal to compare the two for producing a control signal responsive thereto. The control signal is connected to means in said cooling water tower system to cause water to drain therefrom.

DETAILED DESCRIPTION OF THE PREFERRED EMBODIMENT

Figure 1:
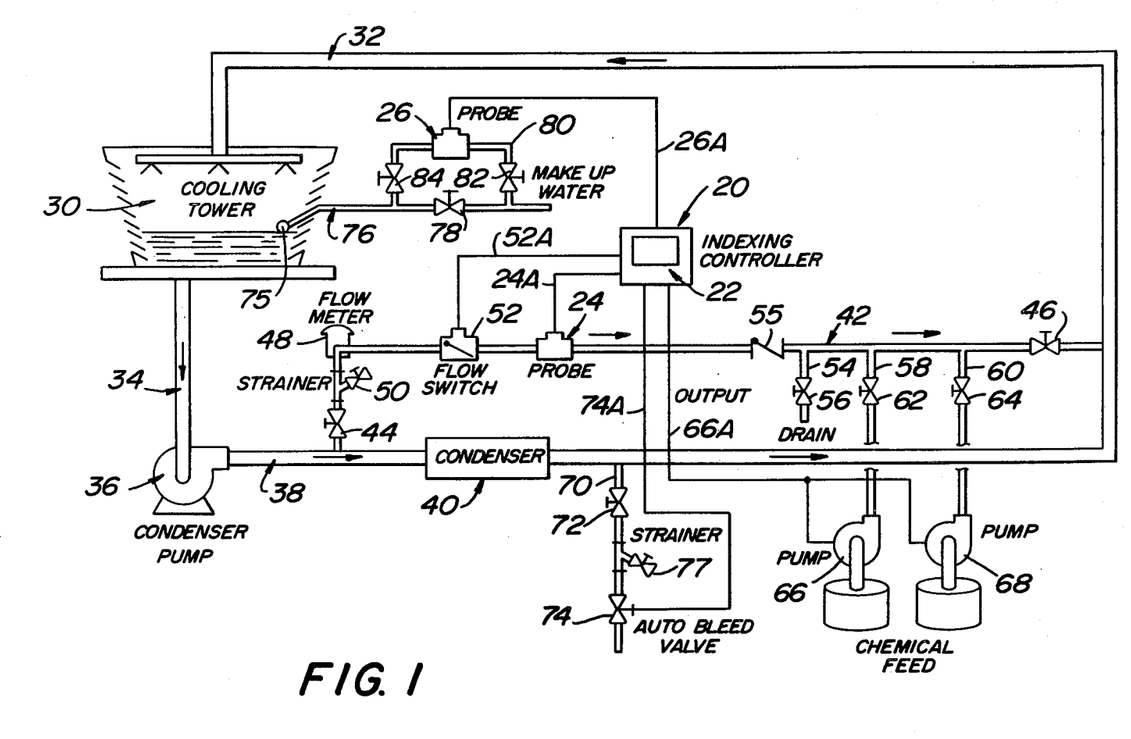
FIG. 1 is a schematic diagram of a typical cooling tower water system and utilizing an indexing controller system constructed in accordance with the instant invention.

Referring now to the various figures of the drawing wherein like reference characters refer to like parts, there is shown at 20 in FIG. 1 an indexing control system constructed in accordance with our invention. The overall system construction and the method of operation of the system is shown and claimed in the copending application of Richard Phillip O'Leary, U.S. patent application Ser. No. 451,356, filed on Dec. 20, 1982, and whose disclosure is incorporated by reference herein.

The indexing controller 20 basically comprises a control unit 22, and a remote pair of probes 24 and 26. The probe 24 is arranged to monitor the conductivity of the water in the cooling tower while probe 26 is provided to monitor the conductivity of the make-up water introduced into the tower.

Before describing the details of the indexing controller system 20, a general description of the cooling tower system is in order. The cooling tower system shown in FIG. 1 is conventional and basically comprises a cooling tower 30 having a water inlet conduit 32 and a water outlet conduit 34. The water outlet conduit 34 is in fluid communication with the input of a condenser pump 36. The output of the pump 36 is connected to a conduit 38 which serves as a inlet to a condenser 40. The outlet of the condenser 40 is connected back to conduit 32. A shunt path 42 is connected across the inlet and outlet of the condenser and enables monitoring of the conductivity of the cooling tower water during operation of the system as well as the introduction of scale retardant chemicals into the cooling tower water system all under the control of the controller system 20.

As can be seen shunt path 42 includes a conventional input valve 44 and a conventional serially connected output valve 46, each of whose function will be described later. The shunt path 42 also includes a conventional flow meter 48, a strainer and associated valve 50, and a flow switch 52, and a check valve 55. The strainer and associated valve 50 serve to trap and flush debris from the system. The flow switch 52 provides a signal via line 52A to the controller to indicate when water is flowing therethrough. The controller uses the signal to prevent the pumps from operating if water isn't flowing. The check valve 55 prevents contamination of the probe by the chemical additives. The probe 24 is located in the path 42 for monitoring the conductivity of the water flowing therethrough and for sending electrical signals indicative thereof, via conductor 24A, to the controller unit 22.

A drain conduit 54 having a valve 56 therein is connected to path 42 to enable water to be drained from shunt 42 when maintenance is to be performed on components in the shunt path. In such a case the valves 44 and 46 are closed. Two chemical inlet feedlines 58 and 60 are connected to path 42 for providing the chemical additives into the system to replace chemicals lost during blow-down. Thus, the feedline 58 includes a manual valve 62 while the feedline 60 includes a manual valve 64. When the valves 62 and 64 are opened chemicals are pumped into the shunt path 42 by the operation of a pair of pumps 66 and 68, respectively under control of the controller unit 22. To that end, each pump receives control signals from the unit 22 via control lines 66A.

The dumping or "blowdown" of water from the system is accomplished through a blowdown or outlet conduit 70. The blowdown conduit is in fluid communication with conduit 32, via a manual valve 72. An automatic bleed valve 74 is located in conduit 72 downstream of manual valve 72. The automatic bleed valve 74 includes a solenoid (not shown) which is electrically connected to the indexing controller 22 via conductor 74A. The solenoid is arranged so that when it is actuated, under the control of the indexing controller, the automatic bleed valve 74 is opened to dump water from conduit 32 to a drain. The strainer and associated valve 77 are provided to trap debris and flush the strainer.

In order to introduce "make-up" water into the cooling tower to replace the water that is dumped during the blowdown and evaporative operation a make-up water inlet conduit 76 is provided connected to a source or sources of make-up water. The inlet conduit 76 includes float valve (not shown) in fluid communication therewith located within the tower. A float 75 is located within the tower and is associated with and controls the operation of the float valve. The inlet conduit 76 also includes a normally closed manual valve 78 which is shunted by a shunt conduit 80. The shunt conduit 80 includes at its inlet a normally open manual valve 82 and at its outlet a normally open manual valve 84. The conductivity sensing probe 26 is located in conduit 80 to sense the conductivity of the water passing therethrough and to provide an electrical signal indicative thereof to the indexing controller 22 via connected conductor 26A.

Operation of the system in FIG. 1 is as follows:

Cooling water is circulated through the path consisting of condenser pump 36, conduit 38, condenser 40, conduit 32, cooling tower 30, and conduit 34. The water which evaporates during operation is automatically replaced with make-up water by the action of the float 75 and its associated valve (not shown). In this regard as the water level in the tower drops due to evaporation the float senses the drop and causes the associated float valve to open, whereupon make-up water flows into the tower. As the water recycles through the system the concentration of minerals in the water increases. The indexing controller system 20 via its probe 24 monitors the electrical conductivity of the tower cooling water, a portion of which flows through the shunt path 42. When the controller system determines that the conductivity of the cooling water in the tower has reached a maximum value (i.e., an adjusted trip point) to maintain a desired Langelier's number a signal is provided by the indexing controller via line 74A to the solenoid of the auto bleed valve 74 to open the valve and cause system water to drain or blow down from the conduit 32. The dropping water level in the tower is sensed by the float and its associated valve is opened to introduce replacement or make-up water from conduit 76. The controller also provides a signal via lines 66A to the chemical pumps to cause them to operate and to introduce replacement chemicals into the system.

The conductivity of the make-up water introduced into the tower is sensed by the probe 26 in the shunt path 80 and a signal indicative thereto is provided via conductor 26A to the indexing controller. The indexing controller utilizes the input signal from probe 26 to calculate the adjusted trip point. When the conductivity of the tower water as sensed by probe 24 drops below the adjusted trip point the controller provides signals to the auto bleed valve and the pumps to cause the former to close and the latter to stop. When sufficient make-up water has been introduced into the tower to compensate for the water dumped the float will have been raised to its normal position and its associated float valve closed to prevent further introduction of make-up water (except for that which is necessary to replace water lost through evaporation). The system is now ready to recirculate the cooling water therethrough until the conductivity of the water in the cooling tower reaches the adjusted trip point as sensed by probe 24, whereupon the blow-down operation as described heretofore reoccurs.

As will be appreciated by those skilled in the art the indexing controller of the instant invention provides an adjusted trip point, that is the system enables the trip point (the maximum concentration for cooling tower water) to be adjusted to reflect changes in conductivity of the make-up water to maintain a desired predetermined Langeliers number or numbers. Thus, even if the make-up water varies substantially in concentration, as could occur if the make-up water is switched from lake water to well water, etc., the desired Langelier's index for the water in the system can be maintained to prevent scaling or corrosion while maximizing the number of cycles that the cooling water can be recirculated before blow-down. That action should be contrasted with the action of prior art conductivity controllers which control blow-down based on a predetermined number of cycles of concentration and not on a predetermined Langelier's Saturation Index. In this regard with prior art controllers one has two options when confronted with varying make-up water conditions, namely, to either establish the trip point based on the maximum number of cycles before scaling would occur with the lowest conductivity of water (thereby running the risk of substantial scaling in the event that higher conductivity make-up water is introduced) or establish the trip point based on the maximum number of cycles for the worst water conditions and control on that number of cycles (and hence blow-down after that same number of cycles for lower conductivity water, an operation that is wasteful of water and chemical additives). Needless to say neither of those choices is viable, particularly if the conductivity of the make-up water changes substantially. Thus, prior art conductivity controllers have substantial limitations when used in applications where the conductivity of the make-up water varies. Unfortunately a large number of municipalies utilize alternate sources of water, which sources frequently vary greatly in conductivity.

The controller system 20 of the instant invention operates to adjust the trip point based upon an indexing factor which takes into account changing water conditions. That indexing factor must be predetermined and is a function of the conductivity of the worst (highest conductivity) and best (lowest conductivity) make-up waters to be introduced into the system and the desired Langelier's number(s) the system is to operate at on both of those sources of water. Thus, one must determine (1) the maximum conductivity for the lowest conductivity (best) make-up water, (2) the maximum conductivity for the highest conductivity (worst) make-up water, (3) the trip point conductivity for the tower when it contains the lowest conductivity water (as calculated for a predetermined Langelier's number), and (4) the trip point conductivity for the tower when it contains the highest conductivity water (as calculated for a predetermined Langelier's number, either the same or different than the first Langelier's number). From these four pieces of data an indexing factor is calculated.

The indexing factor is arrived at by taking the difference between the trip point conductivities of the highest and lowest conductivity waters and dividing that difference by the difference between the make-up water conductivities. Thus, the index factor is defined by the following formula:

Index Factor $= (\text{Tower}_{good} - \text{Tower}_{bad})/(\text{Make-up}_{good} - \text{Make-up}_{bad})$.

To determine the adjusted trip point the controller 22 then takes the calculated index factor and multiplies that factor by the change in conductivity existing in the make-up water supply when referenced to the best (lowest) conductivity make-up water. In this regard, the conductivity actually existing in the make-up conduit is measured and from that value the conductivity of the best make-up water is subtracted. This difference in the make-up water conductivity when multiplied by the index factor defines a delta value which is the change in tower water conductivity necessary to maintain the desired Langelier's number(s). The delta value is referred to herein as the set point number. Inasmuch as the set point number represents a change in tower water to maintain the desired Langeliers number(s), the set point is added to the trip point conductivity of the tower when operating on the best make-up water to produce the adjusted trip point, that is the conductivity of the tower water when utilizing actual make-up water introduced at that moment.

It should be pointed out at this juncture that in calculating the index factor if that factor turns out to be a negative number acid additives should be added to the water or a change in cycles of operation should be made to maintain the same Langelier's Saturation Index (LSI). If no additional acid chemicals are added the cycles of concentration on the highest conductivity water should be lowered to obtain a positive Langelier's saturation index (LSI). If such steps are not taken a different LSI will develop between the two cycles make-up waters and the controller system will maintain an LSI at or between the two LSI's of the cycle make-up waters.

Figure 2:
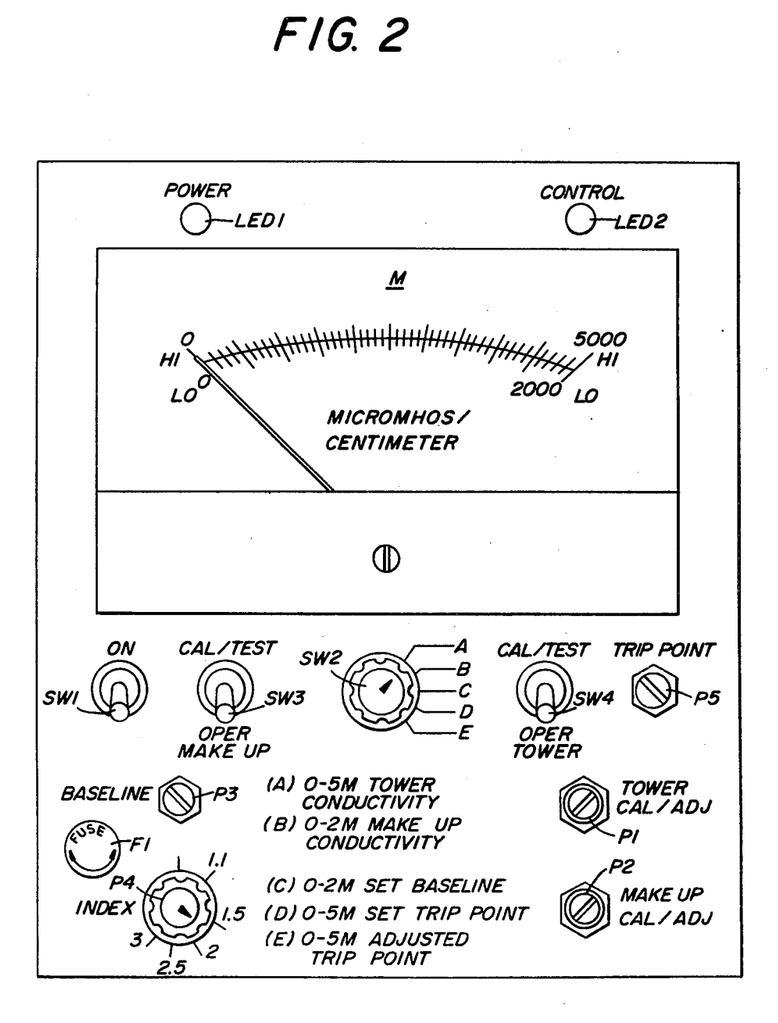
FIG. 2 is a front elevational view of the indexing controller unit shown in FIG. 1.

Referring now to FIG. 2 the construction of the controller unit 22 will be described. Basically the unit comprises a housing including a front panel including plural switches and potentiometers (to be described later) and a meter M which is arranged to display the respective conductivities of the tower and make-up waters. The meter includes two scales, namely, an upper or high scale providing tower water conductivity readings from zero to five thousand (5000) microhmos per centimeter and a lower or low scale providing make-up water conductivity readings from zero to two thousand (2000) microhmos per centimeter.

An on-off switch SW1 is provided on the front panel to enable power to be provided the unit 22. When the unit is powered an LED1 on the upper left hand corner of the front panel is illuminated. When the unit is in its control or operation mode an LED 2 in the opposite corner of the front panel is lit. In the approximate center of the front panel is a five position (A-E) rotary selector switch SW2. Switch SW2 is arranged to select the appropriate function of the unit (as will be described later).

A make-up water switch SW3 is provided on the left hand side of the switch SW2 to enable one to read the conductivity of the make-up water or to calibrate the system to the make-up water conductivity sensing probe 26, depending upon the position of the switch SW3. In the former case the switch SW3 is placed in the down or "operate" position (to be described later) and switch SW2 as in the "B" position. In the latter case the switch SW3 is moved to the upper position and the switch SW2 is in the "B" position. In the calibrate position the meter should deflect to the maximum, i.e., reads two thousand micromhos. If the meter does not read five thousand the instrument has to be calibrated. That calibration is accomplished by a make-up calibrate/adjustment potentiometer P2 having a wiper arm (to be described later) in the form of a slotted head set screw located on the front panel. By adjusting the slotted head screw one can move the meter needle until it is at the desired maximum displacement. Once the needle is at the maximum displacement a shaft lock nut surrounding the set screw is tightened to lock the potentiometer at that setting.

The unit 22 also includes a tower water switch SW4 which is similar to switch SW3. Switch SW4 is used in conjunction with switch SW2 to enable one to read the conductivity of the tower water or to calibrate the system to the tower water conductivity sensing probe 24 depending upon the position of switch SW4 when SW2 is in the "A" position (to be described later). When switch SW4 is in the up position and switch SW2 is in the "A" position the meter needle should deflect to the maximum i.e., read 5000 micromhos. If not the system is calibrated by adjusting a set screw operated potentiometer P1 which is mounted on the front panel in a manner similar to the adjustment of potentiometer P2 described heretofore.

A base line adjustment set screw operated potentiometer P3 is mounted on the front panel of the instrument and is of similar construction of potentiometers P1 and P2. The potentiometer P3 is arranged to establish the conductivity setting for the best (lowest conductivity) make-up water to be introduced into the system from the make-up water supply.

The unit 22 includes a potentiometer P4 to establish the heretofore mentioned indexing factor to enable the control of blow-down operation the cooling system irrespective of changing make-up water conditions. The potentiometer P4 includes a knob which is mounted on the potentiometer shaft in the lower left of the front panel of the unit 22. The potentiometer's knob is arranged to be rotated to a desired numerical index factor which is indicated by a pointer on the knob pointing to numerical indicia on the front panel adjacent the knob.

The unit 22 also includes a trip point adjustment potentiometer P5 mounted on the front panel and of similar construction to the set screw operated potentiometers P1, P2 and P3 described heretofore. The potentiometer P5 establishes a desired trip point (conductivity at which "blow-down" occurs) when the system is operating using the lowest conductivity make-up water.

The unit 22 also includes a fuse F1 for system protection. The fuse is located in a fuse holder in the front panel of the unit.

In order to use the unit 22 it is necessary to predetermine various characteristics of the waters which will be in the cooling tower system. In this regard it is necessary to know the conductivity of the "best" make-up water (lowest conductivity water) which will be introduced into the system, and the conductivity of the "worst" make-up water (highest conductivity water) which will be introduced into the system. It is also necessary to know what the maximum conductivity of the water in the tower should be at a desired Langelier's Saturation Index before blow-down occurs when the system is operating using the best (lowest conductivity) make-up water. Similarly it is necessary to know what the maximum conductivity of the water in the tower should be at a desired Langelier's Saturation Index before blow-down when the system is using the worst (highest conductivity) make-up water. The latter two conductivity figures are each called trip points and each can be calculated in a conventional manner using the Langelier's Saturation Index and a conventional water treatment slide rule or though the use of a computer program.

In accordance with one aspect of my invention one uses these four figures to calculate the numerical index factor which is used to adjust the trip point of the system to take into account changing make-up water conditions. This index factor, once calculated, is dialed onto the potentiometer P4. To calculate the index factor one subtracts the trip point conductivity of the tower water when it consists of the highest (bad) conductivity make-up water from the trip point conductivity of the tower when it consists of the lowest (good) conductivity of make-up water. It should be noted that both of the trip point figures can be based on the same Langelier's number (the most usual situation) or different Langelier's numbers. In any event the index factor is the difference between the two trip-point conductivities divided by the difference between the conductivities for the best (good) and worst (bad) make-up waters as described earlier. The index factor number which is set by potentiometer P4 ensure that the system recycles at the appropriate tower conductivity reading to maintain the desired Langeliers figures(s), irrespective of changes in the make-up water.

The unit 22 must also be provided with data constituting the "baseline" conductivity. This conductivity represents the difference between the conductivity for the lowest conductivity make-up water and the conductivity of the make-up water introduced at that moment. Thus, one substracts the conductivity of the best make-up water from the conductivity of the make-up water being measured by probe 26 at that time. In order to determine the actual make-up water conductivity the rotary switch SW2 is rotated to the "B" position while the make-up water switch SW3 is moved to the "operate" or down position. When switches SW2 and SW3 are in those positions the meter reads the conductivity of the make-up water at that moment as sensed by probe 26. The baseline figure is then set by rotating the switch SW2 to the "C" position. The base line potentiometer P3 is then set by using a screwdriver to rotate its slotted adjustment screw until the meter reading on the low scale equals the baseline value (i.e., calculated difference between the actual make-up water conductivity and the lowest conductivity make-up water). Once the base line has been set the shaft lock nut for potentiometer P3 is tightened to prevent accidental changing of the setting. The trip point (calculated as described heretofore) for the lowest conductivity make-up water must be input into the unit 22 since this figure will serve as the base trip point conductivity which will be adjusted (increased) to reflect the use of make-up water having a conductivity higher than the lowest conductivity make-up water. The adjustment conductivity (i.e., the value added to the base trip point) is equal to the baseline value multiplied by the index factor. To input the trip point into the unit 22 the rotary switch SW2 is rotated to the "D" position and the trip point adjustment potentiometer P5 is rotated via its slotted screw until the meter M provides a reading on the upper scale equal to the base trip point (the trip point for the lowest conductivity water calculated using a predetermined Langelier's number). Once the trip point potentiometer set, the lock nut on the slotted screw is tightened to prevent changing of the setting of the potentiometer.

When the rotary switch SW2 is rotated to the "E" position the unit 22 adjusts the trip point to maintain the desired Langelier's number, irrespective of any change of the make-up water conditions. This adjusted trip point is displayed by the meter M.

As will be described in detail later when the signal provided by probe 24 to the unit 22 indicates that the conductivity of the water in the tower at that moment has reached the adjusted trip point a signal is provided by the unit to the solenoid of the automatic bleed valve 74 to open the valve and thus to dump some tower water to initiate a new cycle of operation.

Figure 3A:
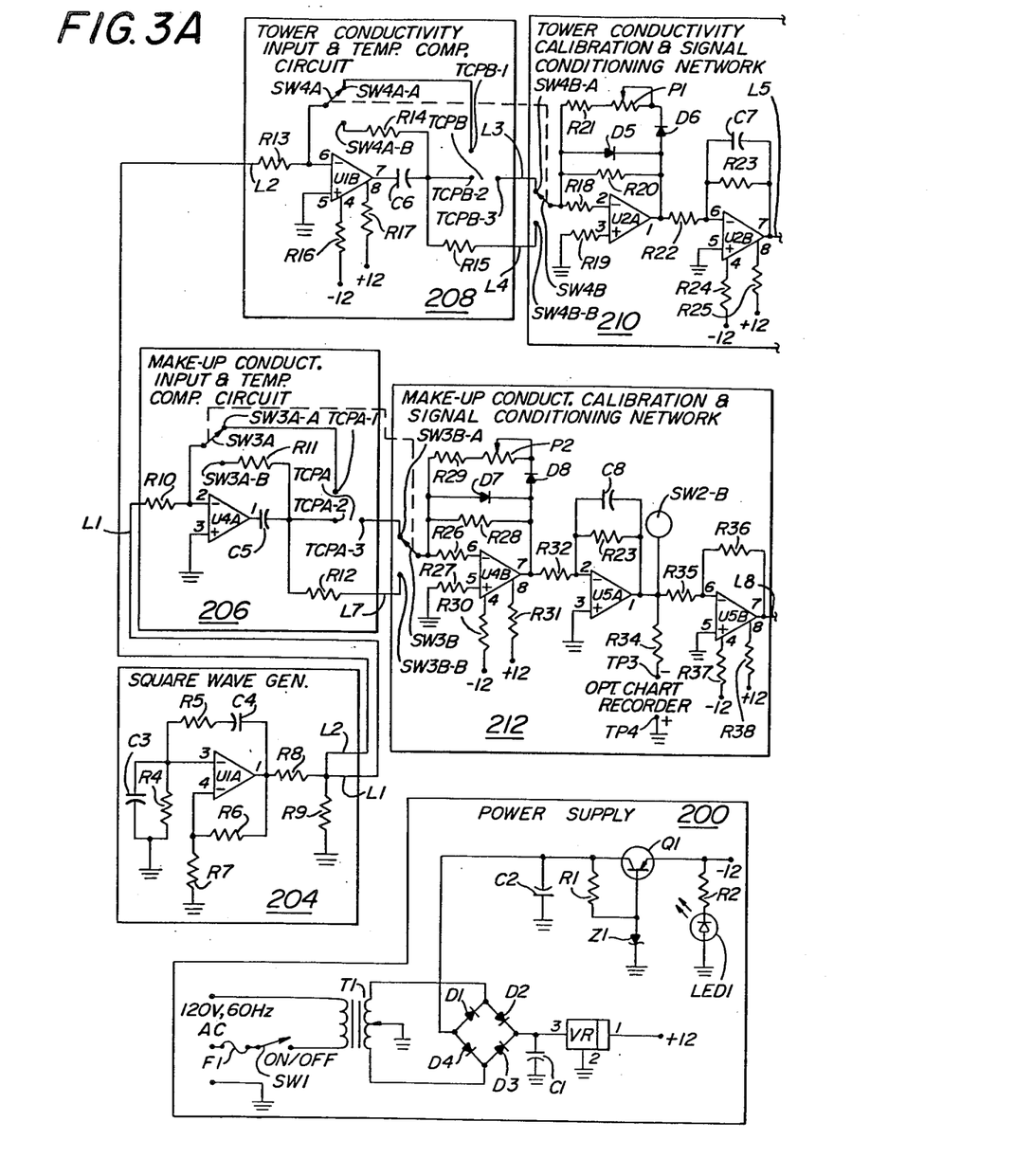
FIG. 3A is a schematic diagram of one portion of the circuitry making up the indexing controller system.
Figure 3B:
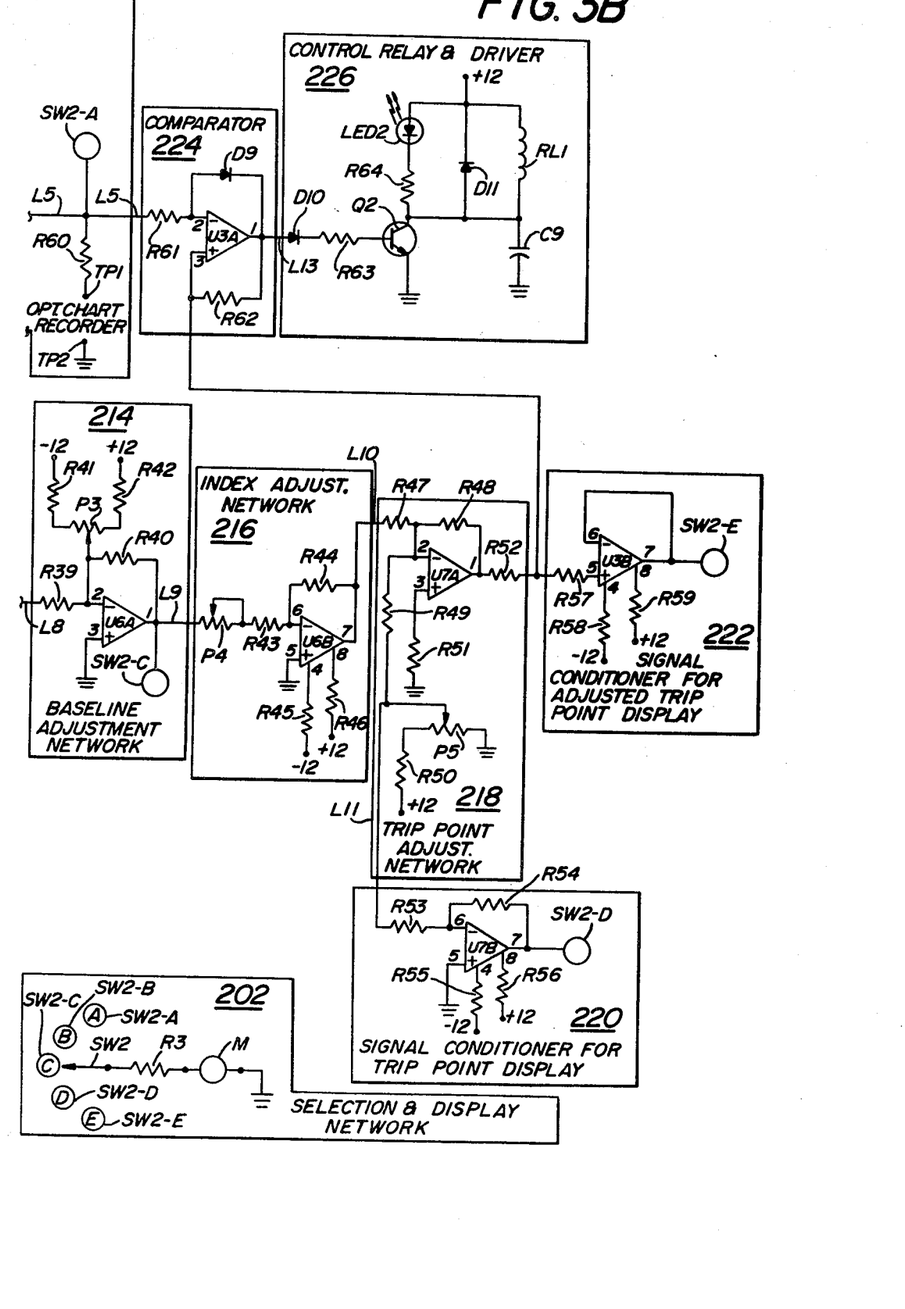
FIG. 3B is a schematic diagram of the remainder of the circuitry of the indexing controller system.

Referring now to FIGS. 3A and 3B the details of the construction of unit 22 will be described.

Basically the unit 22 comprises a power supply circuit 200, a selection and display network 202, a square wave generator circuit 204, a make-up compensation 206, a tower conductivity input and temperature compensation circuit 208, a tower conductivity calibration and signal conditioning network 210, a make-up conductivity calibration and signal conditioning network 212, a baseline adjustment network 214, an index adjustment network 216, a trip point adjustment network 218, a signal conditioner for trip point display circuit 220, a signal conditioner for adjusted trip point display 222, a comparator circuit 224, and a control relay and driver circuit 226.

The power supply circuit 200 is arranged to provide a +12 volts and −12 volts bias to the various electronic and electrical components of the unit from a conventional, i.e., 60 HZ, 120 volts alternating current supply. The power supply 200 basically comprises the heretofore described on/off switch SW1. That switch is connected to one side of the fuse F1. The other side of the fuse is connected to the AC supply. The other side of the switch SW1 is connected to one side of the primary of the transformer T1. The other side of the primary is connected to the other side of the AC supply. The other side of fuse F1 is connected to the other side of the AC supply. The secondary of the transformer T1 includes a grounded center tap. One side of the secondary is connected to the junction of the cathode of diode D1 and the anode of diode D2. The other side of the secondary of the transformer is connected to the common junction of the cathode of diode D4 and the anode of diode D3. The anodes of diode D1 and D4 are connected together as are the cathodes of diodes D2 and D3 to form a DC bridge. The positive side of the bridge is connected to one side of a capacitor C1 and to pin 3 of a conventional integrated circuit voltage regulator VR, e.g., type 78M12. Pin 2 of the voltage regulator VR is connected to ground, while pin 1 is connected to the +12 volt bus. The other side of capacitor C1 is connected to ground. The negative side of the bridge, that is the common junction of the anodes of diodes D1 and D4 is connected to the common junction of one side of filter capacitor C2, one side of a load carrying resistor R1 and the collector of a transistor Q1, e.g., a TN2905A. The other side of capacitor C2 is connected to ground. The other side of resistor R1 is connected to the base of transistor Q1 and to the anode of a zener diode Z1 (such as a 1N759). The cathode of the zener diode is connected to ground. The emitter of transistor Q1 is connected to one side of the resistor R2 and to the −12 volt bus. The other side of the resistor R2 is connected to the cathode of the light emitting diode LED 1. The anode of LED 1 is connected to ground.

As will be appreciated by those skilled in the art, upon the closure of the on/off switch SW1 the AC voltage provided via transformer T1 to the bridge is rectified by the bridge with the resulting voltage being regulated by VR. The negative voltage appearing at the base of transistor Q1 causes the transistor to conduct, whereupon −12 volts is provided onto −12 bus and the LED 1 is illuminated to show that the unit is operating.

The selection and display network 202 basically comprises the heretofore mentioned five position rotary switch SW2 and the meter M. To that end, as can be seen in FIG. 3B switch SW2 includes five contacts, SW2-A, SW2-B, SW2-C, SW2-D, and SW2-E, which correspond to the settings A–E, respectively, shown on the front panel of the instrument. The contacts SW2-A to SW2-E are connected to various circuits of the unit shown in FIGS. 3A and 3B. As can be seen in FIG. 3B the wiper or movable contactor of switch SW2 is connected to one side of a resistor R3. The other side of resistor R3 is connected to one side of the meter M. The other side of the meter M is connected to ground. Thus, depending upon which of the contacts A–E the contactor of switch SW2 contacts the signal at that contact drives the meter to display the system condition for that switch setting.

As described earlier the controller system 20 includes the pair of conductivity probes 24 and 26. Each of the conductivity probes 24 and 26 (sometimes referred to as conductivity cells) are of conventional construction and each is of the temperature compensated type. To that end, each probe includes two carbon electrodes (not shown) and a temperature reference network (not shown). The temperature reference network consists of a resistor, thermister and an associated operational amplifier, with a negative feed-back loop. Gain of the operational amplifier is adjusted to compensate for changes in the temperature of the water since temperature variations have significant effect on the conductivity of the water.

Particularly suitable temperature compensated conductivity probes for use in the system 20 are manufactured and sold by Morr Control, Inc. of Muskogee, Okla. under the model designations TE2A and EH3A. Probe type EH3A is preferrably used for make-up water probe 26 and probe type TE2A is used for the tower water probe 24.

As will be described in detail later, each probe includes a set of three electrical conductors, one conductor going to each of the carbon electrodes and other conductor going to the temperature compensation network. The set of conductors going to the probes from the indexing controller unit 22 are shown schematically in FIG. 1 by reference numerals 26A and 24A. More particularly, schematically shown line 26A represents the conductors connecting the probe 26 to the indexing controller unit 22, while schematically shown line 24A represents the conductors connecting probe 24 to the indexing controller unit 22.

It must be noted that other temperature compensated probes can be utilized in lieu of the types TE2A and EH3A just described.

In any case as is known in order to measure conductivity of water using a temperature compensated probe it is necessary to pass a pulsating electrical signal though the water. Thus, the controller unit 100 includes a square wave generator circuit 204. The square wave generator 204 basically comprises means for producing a 0.5 volt 2000 hz square wave to each of the probes in the system. The square wave generator 204 basically comprises one half of a dual operational amplifier, integrated circuit, such as type LM1458. The half of the integrated circuit making up the square wave generator is denoted by the reference numeral U1A. The circuit 204 also includes a capacitor C3, one side of which is connected to ground and the other side of which is connected to the noninverting input pin 3 of U1A. A resistor R4 is connected in shunt across capacitor C3. The capacitor builds up the charge on pin 3 while the resistor bleeds off the charge, thus establishing the 2000 Hz frequency of circuit 204. The series combination of a resistor R5 and a capacitor C4 is connected as a feed back loop between output pin 1 and the input pin 3. A resistor R6 is connected between output pin 1 and the inverting input pin 2 of U1A. A resistor R7 is connected between pin 2 and ground. The resistors R6 and R7 serve as a voltage divider. The output pin 1 of U1A is connected to one side of resistor R8, the other side of resistor R8, to one side of a resistor R9 and to outputs line L1 and L2. The other side of resistor R9 is connected to ground. Line L2 serves as the input to the tower conductivity input and temperature compensation circuit 208 while line L1 serves as the input to the make-up conductivity input and temperature compensation circuit 206. Thus, the 2000 Hz square wave signal from circuit 204 is provided to both circuits 206 and 208 to provide the necessary pulsating electrical signals for the probes 24 and 26.

The make-up conductivity input and temperature compensation circuit 206 basically comprises a unity gain operational amplifier U4A (composed of one half of another LM1458 integrated circuit) and associated passive components. As can be seen in FIG. 3A input line L1 is connected to one side of a resistor R10. The other side of resistor R10 is connected to inverting input pin 2 of U4A. Pin 2 of U4A is also connected to one moveable contactor SW3A of the heretofore identified make-up switch SW3. That switch SW3 comprises a double pole, double throw switch, having a pair of ganged moveable contactors, SW3A and SW3B, and one pair of stationary contacts SW3-A and SW3A-B in the circuit 206 and another pair of stationary contacts SW3B-A and SW3B-B in the make-up conductivity calibration and signal conditioning network 212.

The non-inverting input pin 3 of U4A is connected to ground. The output pin 1 of U4A is connected to one side of a capacitor C5. The other side of capacitor C5 is connected to the common junction of one side of resistor R11 and one side of precision (calibration) resistor R12 and to one carbon electrode TCPA-2 of the make-up water probe 26 (TCPA). The other side of resistor R11 is connected to stationary switch contact SW3A-B. The temperature compensation connection TCPA-1 of the probe 26 is connected to switch contact SW3A-A. The other side of resistor R12 is connected to line L7. Line L7 serves as the calibration input of the make-up conductivity calibration and signal conditioning network 212. The other electrode TCPA-3 of the probe is connected to line L6 which serves as the operational input to the make-up conductivity calibration and signal conditioning network 212.

When switch SW3 is in the "calibrate" position it's moveable contactor SW3-A is in contact with stationary contact SW3A-B. The square wave signal appearing on line 1 produces a predetermined voltage across the precision resistor R12 which voltage is indicative of a full scale deflection of the meter needle i.e., a reading of 2000 micromhos.

When the switch SW3 contactor SW3-A is in the "operating" position its contactor SW3A is in contact with stationary contact SW3A-A so that the 2000 Hz signal is provided to the temperature compensation input TCPA-1 of the probe while the operational amplifier provides the 2000 Hz square waves to the electrode TCPA-2. The 2000 Hz square waves are introduced into the make-up water and through it to electrode TCPA-3. Thus, the signal appearing on line L6 is indicative of the measured conductivity of the water. The water conductivity signal is provided from line L6 though the ganged movable contactor SW3-B of switch SW3 into the make-up conductivity calibration and signal conditioning network 212.

When the switch SW3 is in the calibrate or test position the signal appearing on L7 (which is indicative of a full scale deflection) is provided via the stationary switch contact SW3B-B and moveable contactor SW3-B to the input of the make-up conductivity calibration and signal conditioning network 212.

The tower conductivity input and temperature compensation circuit 208 is similar in construction to the make-up conductivity input and temperature compensation circuit 206. To that end, as can be seen input line L2 to the circuit 208 is connected to one side of a resistor R13. The other side of resistor R13 is connected to pin 6 an inverting unity gain amplifier U1B. U1B constitutes the other half of the dual integrated circuit which makes up UIA in circuit 204. Pin 5 of U1B is connected to ground. Pin 4 is connected to one side of a bias resistor R16, the other side of which is connected to −12 volt bus, while pin 8 is connected to one side of bias resistor R17, the other side of which is connected to the +12 voltage bus. Pin 6 of UIB is connected to a movable contactor SW4A forming a part of the tower switch SW4. Switch SW4 like switch SW3, is a double pole, double throw, ganged switch. Thus, SW4 includes a pair of stationary contacts SW4A-A and SW4A-B. Contact SW4A-A is connected to the temperature compensating lead TCPB-1 of the tower conductivity probe 24 (TCPB) while stationary contact SW4A-B is connected to one side of resistor R14. The other side of resistor R14 is connected to the common juncture of one side of capacitor C6, one side of a precision resistor R15 and electrode TCPB-2 of the tower probe 24. The other side of capacitor C6 is connected to pin 7, the output pin of the operational amplifier U1B. The other electrode, TCPB-3 of probe 24 is connected to output line L3. This line serves as the operational input to the tower conductivity calibration and signal conditioning network 210. The other side of resistor R15 of circuit 208 is connected to line L4 which serves as the calibrate input line to the circuit 210.

As will be appreciated by those skilled in the art, tower conductivity input and temperature compensation circuit 208 operates in a similar manner to circuit 206. Thus, when switch SW4 is in the calibrate position the signal provided by the precision resistor R15 to line L4 is indicative of a full scale deflection (i.e., 5000 micromhos) of the meter. This signal is provided through the stationary contact SW4B-B and movable contactor SW4B-B of switch SW4 to circuit 210. When the switch 4 is in the operate position, like that shown in FIG. 3, the voltage produced across the electrodes of the probe is provided via line L3, stationary contact SW4B-A and switch contactor SW4B to the input of the tower conductivity calibration and signal conditioning network 210.

The tower conductivity calibration and signal conditioning network 210 serves to take the input signal from either the probe 24 (via line L3) or the calibrate line L4 and to calibrate it to the meter's scale for the water conductivity. Thus, circuit 210 basically comprises a first stage operational amplifier U2A and a second stage operational amplifier U2B. The two stages are formed by a LM1458 dual integrated circuit. The first stage of the dual circuit, that is operational amplifier U2A, is provided with the input from the tower conductivity input and temperature compensation circuit 208. To that end, the movable contactor SW4B of switch SW4 is connected to the common junction of one side of a current limiting resistor R18, one side of a feedback resistor R20, the anode of a diode D5 and one side of a feedback resistor R21. The other side of resistor R18 is connected to pin 2, the inverting pin, of U2A. The other side of resistor R20 is connected to output pin 1 of U2A. The cathode of diode D5 is connected to the common junction of the anode of a diode D6 and to pin 1 of U2A. The cathode of diode D6 is connected to one side of the tower cal/adjust potentiometer P1 and to its wiper arm (set screw). The other side of potentiometer P1 is connected to the other side of resistor R21. Pin 3 of U2A is connected to one side of a resistor R19, the other side of which is connected to ground. One side of resistor R22 is connected to pin 1 of U2A and the other side of resistor R22 is connected to pin 6, the inverting input of pin of the second stage U2B. Pin 6 is also connected to one side of a feedback resistor R23 and to one side of a capacitor C7. The other side of capacitor C7 and the other side of resistor R23 are connected together to output pin 7 of U2B. Pin 7 is also connected to output line L5 and to the common junction of stationary switch contact SW2-A and one side of a current limiting resistor R60. The other side of resistor R60 is connected to a test point TP1 which serves as one connector for an optional strip chart recorder. Another test point TP2 is provided to serve as another connector for the optional strip chart recorder. TP2 is connected to ground. Pin 5 of U2B is connected to ground. Pin 4 of U2B is connected to one side of a bias resistor R24 the other side of which is connected to the −12 volt bus, while pin 8 is connected to one side of bias resistor R25, the other side of which is connected to +12 volt bus.

Operation of the tower conductivity calibration and signal conditioning network 210 is as follows: When the five position selector switch SW2 is in the "A" position and switch SW4 is in the calibrate/test position its movable conductor SW4B is in electrical contact with stationary contact SW4B-B, whereupon the signal appearing on line L4, which should result in a full scale deflection of the meter needle is provided via resistor R18 to the inverting input pin 2 of U2A. The operational amplifier amplifies the signal in accordance with the setting of P1. The resulting signal is also amplified by U2B and passes through switch contact SW2-A to the meter M. At full scale deflection the output signal is −5 volts DC. If the meter needle does not deflect fully the potentiometer P1 is then adjusted (as described earlier) to cause the meter's needle to move to the full scale deflected position, i.e., 5000 micromhos.

The make-up conductivity calibration and signal conditioning network 212 is similar in construction and operation to circuit 210 just described. To that end, circuit 212 includes a pair of operational amplifiers U4B and U5A, which are connected and operate similarly to U2A and U2B, respectively. U4A constitutes one half of the integrated circuit forming U4A of circuit 206, while U5A constitutes one half of an dual LM1458 integrated circuit. The other half of that integated circuit makes up operational amplifier U5B in circuit 212 (to be described later).

As can be seen in FIG. 3A the movable contactor SW3B of SW3 is connected to the common juncture of one side of resistor R26, one side of a feedback resistor R28, the anode of diode D7, and one side of resistor R29. The other side of resistor R26 is connected to pin 6, the inverting input pin of U4B. The non-inverting input pin, that is pin 5 of U4B, is connected to one side of a resistor R27, the other side of which is connected to ground. The other side of resistor R28 is connected to the common junction of the cathode of diode D7, the anode of diode D8, output pin 7 of U4B, and one side of a resistor R32. The cathode of diode D8 is connected to the common junction of one side of the make-up calibrate/adjust potentiometer P2 and its wiper arm (set screw). The other side of potentiometer P2 is connected to the other side of a resistor R29. Pin 4 of U4B is connected to one side of bias resistor R30, the other side of which is connected to the −12 volt bus, while pin 8 is connected to one side of a bias resistor R31, the other side of which is connected to the +12 volt bus. The other side of resistor R32 is connected to the common junction of the inverting input pin 2 of U5A, one side of a resistor R33 and one side of a capacitor C8. The other side of capacitor C8 and the other side of resistor R33 are connected together to the output pin 1 of U5A and to the common junction of switch contact SW2-B, one side of a resistor R34 and one side of a resistor R35. The other side of resistor R34 is connected to test point connector TP3. Test point TP3 is arranged to be connected to one side of an optional chart recorder. Another test point TP4, for connection to the optional chart recorder, is provided in circuit 212 and is connected to ground. The other side of resistor R35 is connected to the inverting input pin 6 of a unity gain operational amplifier U5B. This amplifier serves to invert the DC signal appearing at its input to provide a 0 to +5 volt DC signal at its output LIne L8 (+5 volts for full scale deflection). Thus, pin 6 of U5B is connected to one side of feedback resistor R36, the other side of which is connected to pin 7, the output pin of U5B and to line L8. Pin 5 of U5B is connected to ground. Pin 4 of U5B is connected to one side of a resistor R37, the other side of which is connected to the −12 volt bus, while pin 8 is connected to one side of a resistor R38, the other side of which is connected to the +12 volt bus.

As will be appreciated by those skilled in the art, the output signal appearing on line L8 from the make-up conductivity calibration and signal conditioning network 212 is a DC signal similar to the signal appearing on L5 from the tower conductivity calibration and signal conditioning network 210 but of opposite polarity. In particular the DC output signal is indicative of the existing conductivity of the make-up water as determined by the test probe 26. When switch SW2 is in the "B" position this signal passes through stationary contact SW2-B and moveable contactor of SW2 to the meter to cause the meter's needle to deflect to provide a reading of the make-up conductivity.

The DC signal indicative of conductivity of the make-up water is also provided as an input to the base line adjustment network as shown in FIG. 3B. As can be seen therein network 214 basically comprises an operational amplifier U6A which forms one half of a LM1458 dual integrated circuit. Input line L8 is connected to one side of a resistor R39. The other side of resistor R39 is connected to the common junction of inverting input pin 2 of U6A, one side of of a feedback resistor R40 and to the wiper arm (set screw) of base line adjusting potentiometer P3. The other side of resistor R40 is connected to the common junction of output pin 1 of U6A, output line L9 and switch SW2-C of switch SW2. The non-inverting input pin 3 of the operational amplifier U6A is connected to ground. The −12 volt bus is connected to one side of a resistor R41, the other side of which is connected to one side of the potentiometer P3. The other side of potentiometer P3 is connected to one side of a resistor R42, the other side of which is connected to the +12 volt bus. The resistors R41 and R42 serve to reduce the bias voltage to appropriate 0 to +5 volt levels. As will be appreciated by those skilled in the art the operational amplifier U6A serves to provide a signal which is equal to the algebraic difference between the DC signal appearing on line L8 (indicative of make-up water conductivity) and the signal appearing across potentiometer P3. The latter signal represents the conductivity of the lowest conductivity make-up water which is input by adjusting P3 as described earlier and is displayed by meter M through switch SW2-C. In particular when the rotaty switch SW2 is in the "C" position its movable contactor is in contact with SW2-C of the base line adjustment network, whereupon the signal appearing on line L9 which is indicative of the adjusted base line is provided resistor via R3 to the meter for display thereof.

The output signal appearing on line L9 is also provided to the index adjustment network 216. This circuit is arranged to multiply the base line value (the difference between the measured make-up conductivity and the lowest conductivity of the make-up water) by the numerical index factor (calculated using the formula described heretofore) to produce the adjusted base line value (which represents the change in the tower water necessary to maintain the desired Langelier's number) and to provide the same to the trip point adjustment network 218.

The index adjustment network 216 basically comprises an inverting operational amplifier U6B which is formed of the other half of the integrated circuit making up operational amplifier U6A of circuit 214. Input line L9 is connected to one side of the index adjustment potentiometer P4. The other side of potentiometer P4 is connected to the common junction of one side of a resistor R43 and the wiper arm (set screw) of potentiometer P4. The other side of resistor R43 is connected to the common junction of one side of a feedback resistor R44 and the inverting input pin 6 of U6B. The non-inverting input pin 5 of U6B is connected to ground. The other side of resistor R44 is connected to output pin 7 of U6B and to output line L10. Pin 4 of U6B is connected to one side of a bias resistor R45, the other side of which is connected to the −12 volt bus, while pin 8 is connected to one side of a resistor R46, the other side of which is connected to the +12 volt bus. The setting of the index potentionmeter P4 establishes the multiple or index factor. The resistances of R43 and R44 are set so that the output signal appearing on line L10 and which represents the product of the index factor and the base line conductivity (and hence is read on the meter's lower scale) is properly proportioned for subsequent addition to the tower trip point conductivity which is read off of the upper scale of the meter. This addition is accomplished in the trip point adjustment network. The output signal of circuit 216 is a negative DC voltage from 0 to −5 volts, depending upon water conditions.

As can be seen the trip point adjustment network 218 basically comprises a unity gain, summing amplifier U7A which comprises one-half of a LM1458 dual integrated circuit. Input line L10 is connected to one side of a summing resistor R47, the other side of which is connected to one side of feedback resistor R48, to one side of another summing resistor R49 and to the inverting input pin 2 of U7A. The other side of resistor R49 is connected to the wiper arm (set screw) of the trip point potentiometer P5 and to line L11 from the signal conditioner for trip point display circuit 220. One side of the potentiometer P5 is connected to one said of a resistor R50, the other side of which is connected to the +12 volt bus. The other side of potentionmeter P5 is connected to ground. One side of a resistor R51 is connected to the non-inverting input pin 3 of U7A, while the other side of the resistor is connected to ground. The other side of feedback resistor R48 is connected to the common junction of output pin 1 of U7A and to one side of an output resistor R52. The other side of resistor R52 is connected to output lines L12.

The appropriate setting of potentiometer P5, as described earlier, establishes a DC signal indicative of the predetermined conductivity for the tower water when the system operates on the best water (the lowest conductivity water). The circuit U7A acts as a summing amplifier to provide a signal which is indicative of the sum of the adjusted base line signal (provided by circuit 216) and the tower trip point conductivity for best water conditions (as set by P5).

In order to condition the signal produced by potentiometer P5 so that meter m can accurately display the trip point conductivity, the signal conditioner for trip point display circuit 220 is provided. This circuit serves to invert the DC Voltage produced by potentiometer P5 so that it is of appropriate polarity for the meter and then to provide it to the meter via switch SW2. To that end the circuit 220 basically comprises inverting amplifier U7B. U7B constitutes the other half of the integrated circuit forming U7A. Line L11 is connected to one side of an input resistor R53. The other side of resistor R53 is connected to the common junction of inverting input pin 6 of U7B and to one side of a feedback resistor R54. The other side of the feedback resistor is connected to output pin 7 of U7B and to switch contact SW2-D of switch SW2. The non-inverting input pin 5 of U7B is connected to ground. Pin 4 of U7B is connected to one side of the resistor R55, the other side of which is connected to the −12 volt bus, while pin 8 is connected to one side of resistor R56, the other side of which is connected to the +12 volt bus.

Since line L11 is connected to the wiper arm (set screw) of potentiometer P5 the DC Signal provided by the potentiometer is fed to the inverting amplifier U7B. The signal is inverted and provided at output contact SW2-D of SW2 for display on meter M when selector switch SW2 is in the "D" position.

The adjusted trip point output signal of the trip point adjustment network 218 is provided via line L12 as one input to the comparator circuit 224 (to be described later) and also as an input to the signal conditioner for adjusted trip point display circuit 222. The latter circuit basically comprises a voltage follower operational amplifier U3B, which constitutes one half of the integrated circuit making up operational amplifier U3A in the comparator. Input line L12 to the circuit 222 is connected to one side of resistor R57. The other side of resistor R57 is connected to pin 5, the non-inverting input pin, of U3B. The inverting input pin 6 of U3B is directly connected to output pin 7 and to switch contact SW2-E of switch SW2. Pin 4 of U3B is connected to one side of bias resistor R58, the other side of which is connected to the −12 volt bus, while pin 8 is connected to one side of a bias resistor R59, the other side of which is connected to +12 volt bus. The circuit 222 is arranged to condition the signal indicitive of the adjusted trip point so that when it is provided via switch contact SW2-E and resistor R3, to the meter M it does not load the circuitry down.

The comparator 224 basically comprises operational amplifier U3A which constitutes the other half of the integrated circuit forming U3B in circuit 222. The comparator serves to compare the signals appearing on lines L5 and L12. Thus, line L5 from the tower conductivity calibration and signal conditioning network 210 is connected to one side of a resistor R61. The other side of resistor R61 is connected to the common junction of the anode of a diode D9 and the inverting input pin 2 of U3A. The cathode of diode D9 is connected to pin 1, the output pin of U3A, to one side of a resistor R62 and to output line L13. The other side of resistor R62 is connected to the non-inverting input pin 3 of the U3A and to input line L12. Thus, as will be appreciated by those skilled in the art when the voltage appearing on line L5 reaches the voltage appearing on line L12 U3A turns on to provide a positive DC output signal on line L13 to the control relay and driver circuit 226. This signal intiates the blow-down cycle.

The control relay and driver circuit 226 is arranged to actuate the relay of the auto bleed valve 74 to effect the dumping of the cooling water when the comparator senses that the tower water has achieved the adjusted trip point conductivity. The control relay and driver circuit 226 basically comprises a diode D10, whose anode is connected to input line L13. The cathode of diode D10 is connected to one side of a resistor R63. The other side of resistor R63 is connected to the base of a transistor Q2, such as a TN2219. The emitter of transistor Q2 is connected to ground. The collector of transistor Q2 is connected to the common junction of one side of a resistor R64, the anode of a diode D11, one side of a relay coil RL1 and one side of a capacitor C9. The other side of capacitor C9 is connected to ground. The other side of resistor R64 is connected to the cathode of a light emitting diode LED 2. The anode of LED 2 is connected to the common juncture of the +12 volt bus, the cathode of diode D11 and the other side of relay coil RL1. Associated with relay coil RL1 are a normally open pair of contacts (not shown) and a normally closed pair of contacts (not shown) in the auto bleed valve's solenoid circuit 74.

As will be appreciated by those skilled in the art when the signal appearing on line L13 indicates that the tower water conductivity has reached the adjusted trip point the signal provided via diode D10 and resistor R63 to the base of transistor Q2 causes the transistor to conduct. This action causes the +12 volts bias to appear across relay coil RL1 to energize the coil and cause its associated relay contacts to close. This action causes the auto bleed valve 74 to open. At the same time the light emitting diode LED 2 illuminates.

As will be appreciated by those skilled in the art when the cooling tower water sensing probe 24 returns the signal, via circuits 208 and 210, to the comparator 224, which signal is below the adjusted trip point signal (as provided from circuit 218 and which changes with the introduction of the make-up water), a positive voltage no longer appears on line L13. This action causes the transistor Q2 in control relay and driver circuit 226 to cease conducting, whereupon relay coil RL1 is de-energized. The de-energization of relay coil RL1 causes the solenoid in the auto bleed valve 74 to close, thereby ceasing the dumping of water through the auto bleed valve. At the same time the pumps 66 and 68 are disabled by the signal appearing on line 66A.

As should be appreciated by the foregoing the apparatus of instant invention is a continuously operative, proportional, indexing, cooling water conductivity computer/controller which determines the proper saturation index and chemical feed necessary for the cooling system, while maximizing water conservation and cooling water corrosion control. In particular, the system comprises simple, yet effective dual-probe conductivity sensors and associated electronic control means that adjusts and controls the tower blow-down and chemical feed through proportional indexing of make-up water and tower water charactertistics and based on desired Langelier's number(s). In this regard the sensor probe in the make-up water supply line sends a signal to the controller which is proportionally reset against the desired set point. The controller then reads variations in make-up water charactertistics which are normally recalculated and compared against the tower water conductivity as sensed by the other conductivity probe. The controller then adjusts both chemical feed and blow-down for specific changes in make-up water supply.

The method provides a way of determining an index factor to be used by the controller to effect accurate proportional indexing to maintain a desired Langelier's number(s) irrespective of changing make-up water conditions.

Without further elaboration the foregoing will so fully illustrate my invention that others may be applying current or future knowledge readily adapt the same for use under various conditions of service.

We claim:

1. A solid state control system for use in a cooling tower water system having a supply of make-up water and means for enabling water to be drained from said system, said control system comprising signal generating means for producing a periodic signal, first conductivity sensing probe means coupled to said signal generating means and adapted for disposition in the cooling tower water to provide a first signal proportional to the conductivity of the tower water, second conductivity sensing probe means coupled to said signal generating means and adapted for dispostion in the make-up water supply to said cooling tower to provide a second signal proportional to the conductivity of the make-up water, display means for displaying system water conductivities, first and second selectively actualable calibration means for calibrating said display means to said first conductivity sensing probe means and said second conductivity sensing probe means, respectively, selector switch means for selectively providing signals produced by said controller system to said display means to display conductivity readings, third circuit means having first and second inputs, said first input being coupled to said second conductivity sensing probe for receipt of said second signal, said second input comprising an adjustable signal, said third circuit means subtracting said second signal from said first signal to produce a delta signal, said delta signal being coupled, via said selector switch means to said display means to display said delta signal, fourth circuit means connected to said third circuit means and including fourth selectively adjustable means for producing a product signal equal to the product of said delta signal and a value established by said fourth selectively adjustable means, fifth circuit means connected to said fourth circuit means and said selector switch means and having a pair of inputs and fifth selectively adjustable means for producing a fifth signal, said fifth signal serving as one of said inputs and said product signal serving as the other of said inputs, said fifth circuit means adding the input signals to produce an output signal, said output signal being coupled by said selector switch means to said display means to display said output signal, comparator means connected to said fifth circuit means for receipt of said output signal and also arranged for receipt of said first signal to compare said output signal to said first signal to produce a control signal responsive thereto, said control signal being connected to means in said cooling water tower system to cause water to drain therefrom.

2. The system of claim 1 wherein said display means comprises a meter.

3. The control system of claim 2 wherein said first and second conductivity sensing probe means, each comprise a temperature compensated conductivity cell.

4. The control system of claim 1 wherein said first and second calibration means each produce a signal which effects a respective predetermined conductivity reading by said meter.

5. The control system of claim 1 additionally comprising signal conditioning means for conditioning the signal provided to the display means.

6. The control system of claim 1 wherein said signal generation means comprises means for producing a cyclical square wave.

7. The control system of claim 1 wherein said first selectively actuable calibration means comprises first switch means for selectively coupling said first calibration means to either said first conductivity sensing probe means or to first reference signal supplying means, said first reference signal supply means providing a first reference signal to calibrate said first conductivity sensing probe means.

8. The control system of claim 7 comprising operational amplifier means for selective receipt of either said first signal or said first reference signal.

9. The control system of claim 8 additionally comprising variable resistance means for adjusting the gain of said amplifier so that said display means displays a predetermined reading when the signal provided to said operational amplifier comprises said first reference signal.

10. The control system of claim 1 wherein said second selectively actuable calibration means comprises second switch means for selectively coupling said second calibration means to said second conductivity sensing probe means or to second reference signal supplying means, said second reference signal supply means providing a second reference signal to calibrate said second conductivity sensing probe means.

11. The control system of claim 10 comprising operational amplifier means for selective receipt of either said second signal or said second reference signal.

12. The control system of claim 11 additionally comprising variable resistance means for adjusting the gain of said amplifier so that said display means displays a predetermined reading when the signal provided to said operational amplifier comprises said second reference signal.

13. The control system of claim 1 wherein said third circuit means comprises an operational amplifier for receipt of said first first and second inputs and wherein said third circuit comprises variable resistance means for establishing said second input.

14. The control system of claim 1 wherein said fourth circuit means comprises an operational amplifier and variable resistance means, said delta signal being provided to said variable resistance means.

15. The control system of claim 1 wherein said fifth circuit means comprises an operational amplifier arranged to sum the first and second input signals, said fifth selectively adjustable means for producing said second input signal comprising variable resistance means.

* * * * *

UNITED STATES PATENT AND TRADEMARK OFFICE
CERTIFICATE OF CORRECTION

PATENT NO. : 4,460,008

DATED : July 17, 1984

INVENTOR(S) : Richard P. O'Leary and Robert V. Morris

It is certified that error appears in the above-identified patent and that said Letters Patent are hereby corrected as shown below: On the title page Item [73] should read: --- Betz Entec, Inc., Horsham, Pennsylvania. ---

Signed and Sealed this

Ninth Day of July 1985

[SEAL]

*Attest:*

DONALD J. QUIGG

*Attesting Officer*     *Acting Commissioner of Patents and Trademarks*